United States Patent [19]

Tanabe et al.

[11] 4,156,685

[45] May 29, 1979

[54] PROCESS FOR PRODUCING A HYDROFURAN AND A 1,4-DIOL

[75] Inventors: Yasuo Tanabe, Tokyo; Jun Toriya, Kurashiki; Ikuo Kasahara, Kurashiki; Ken Shiraga, Kurashiki, all of Japan

[73] Assignee: Mitsubishi Chemical Industries Limited, Tokyo, Japan

[21] Appl. No.: 928,429

[22] Filed: Jul. 27, 1978

[30] Foreign Application Priority Data

Aug. 3, 1977 [JP] Japan .................................. 52/93224

[51] Int. Cl.$^2$ ..................... C07C 27/02; C07D 307/08
[52] U.S. Cl. ............................... 260/346.11; 568/851; 568/858
[58] Field of Search .................. 260/346.11; 568/857, 568/858

[56] References Cited

U.S. PATENT DOCUMENTS

| | | | |
|---|---|---|---|
| 4,005,112 | 1/1977 | Smith | 260/346.11 |
| 4,005,113 | 1/1977 | Smith | 260/346.11 |
| 4,010,171 | 3/1977 | Smith | 260/346.11 |
| 4,010,197 | 3/1977 | Toriya et al. | 260/491 |
| 4,011,244 | 3/1977 | Smith | 260/346.11 |

FOREIGN PATENT DOCUMENTS 2062950 7/1971 Fed. Rep. of Germany.
2645030 4/1977 Fed. Rep. of Germany.

*Primary Examiner*—Richard Raymond
*Attorney, Agent, or Firm*—Bierman & Bierman

[57] ABSTRACT

A process is disclosed in which hydrolysis and cyclization of an acetate ester of a 1,4-diol are carried out in separate reaction zones in the pressure of a solid acid catalyst and unreacted acetate ester recovered from each of the reaction zones is supplied to another zone thereby producing a hydrofuran and a 1,4-diol in any proportion.

8 Claims, 5 Drawing Figures

PROCESS FOR PRODUCING A HYDROFURAN AND A 1,4-DIOL

FIELD OF THE INVENTION

This invention relates to a process for producing a hydrofuran and a 1,4-diol simultaneously from an acetate ester of a 1,4-diol and, in particular, a commercial process for producing tetrahydrofuran and 1,4-butanediol simultaneously and in any proportion by reacting an acetate ester of 1,4-butanediol with water in the presence of a solid acid catalyst.

BACKGROUND OF THE INVENTION

Both 1,4-butanediol and tetrahydrofuran are useful as a solvent and raw materials for organic synthesis such as polymeric material. They have been produced through various ways. For example, tetrahydrofuran is produced by (a) catalytic hydrogenation of furan which has been obtained by elimination of carbonyl group from furfural, (b) dehydration cyclization of butanediol obtained by hydrogenation of butynediol which is a reaction product of acetylene and formaldehyde and (c) reaction of 1,4-diacetoxybutanediol and water in the presence of an acid catalyst; and 1,4-butanediol is produced by (d) hydrogenation of butynediol and (e) hydrolysis of 1,4-diacetoxybutane.

The production of 1,4-butanediol by hydrolysis of 1,4-diacetoxybutane and the production of tetrahydrofuran by cyclization of 1,4-diacetoxybutane with elimination of acetic acid belong to entirely different category of reactions as follows.

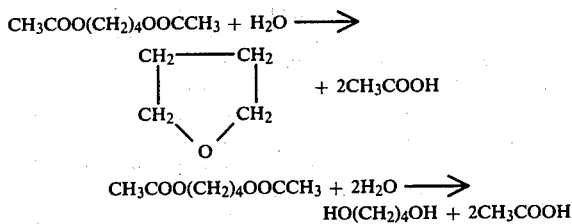

$$CH_3COO(CH_2)_4OOCCH_3 + 2H_2O \longrightarrow$$
$$HO(CH_2)_4OH + 2CH_3COOH$$

Thus, hitherto in producing 1,4-butanediol and tetrahydrofuran from 1,4-diacetoxybutane, both reactions have been carried out in separate reaction systems.

It has been found that, in the case where 1,4-butanediol and tetrahydrofuran are produced from an acetate ester of 1,4-butanediol in a single reaction zone containing a solid acid catalyst, the proportion of 1,4-butanediol and tetrahydrofuran is closely correlated with the reaction temperature, the liquid hourly space velocity (LHSV) of the acetate ester of 1,4-diol supplied to the reaction zone, the amount of the reaction product to be supplied to distillation column from which the 1,4-diol product is recovered and the amount of the reaction product to be circulated to the reaction zone. For example, the higher the reaction temperature, the higher the reaction rate at which the hydrofuran is produced; at a lower reaction temperature such as at 50° C., the production of hydrofuran increases with an increase in the LHSV, and with an increase in the amount of the reaction product to be supplied to the separation column the amount of 1,4-diol product increases.

However, the hydrolysis reaction for producing 1,4-diol is preferably carried out with a high water content; on the other hand, the cyclization reaction is conveniently effected with a low water content. Thus, it is difficult to conduct two such different types of reaction in a single reaction zone at high efficiency.

It has been found that hydrolysis of 1,4-diacetoxybutane and cyclization of 1,4-diacetoxybutane with elimination of acetic acid can be carried out in separate reaction zones by circulating unreacted raw material recovered from each of the reaction zones to another zone, whereby the desired diol and cyclic ether are obtained with high efficiency and in any proportion, since the proportion may readily be changed as required.

SUMMARY OF THE INVENTION

Accordingly, a main object of this invention is to provide a process for producing a 1,4-diol and a hydrofuran simultaneously from an acetate ester of a 1,4-diol.

Another object is to provide a commercially beneficial process for producing a 1,4-diol and a hydrofuran simultaneously and in any proportion from an acetate ester of a 1,4-diol.

Still another object is to provide a process for producing 1,4-butanediol and tetrahydrofuran simultaneously from 1,4-diacetoxybutane.

A further object is to provide a process for producing 1,4-butenediol and dihydrofuran from 1,4-diacetoxybutene.

According to this invention there is provided a process wherein an acetate ester of 1,4-butanediol or 1,4-butenediol is reacted with water in the presence of a solid acid catalyst to produce a corresponding cyclic ether and a corresponding diol, the improvement comprises the steps of:

(a) supplying the bottom fraction containing an acetate ester of a 1,4-diol from step (d) and water to a first reaction zone containing a solid acid catalyst to obtain a corresponding 1,4-diol, (b) supplying the reaction production to a first distillation column to distil out water and acetic acid and to obtain a bottom fraction containing the diol and the acetate ester, (c) supplying optionally a portion of the bottom fraction to a second distillation column to recover the diol as a bottom fraction and supplying the top fraction containing the acetate ester of 1,4-diol from the second column together with the rest of the bottom fraction from the first distillation column to a second reaction zone containing a solid acid catalyst to obtain a corresponding cyclic ether, (d) supplying the reaction product to a third distillation column to obtain a bottom fraction containing the diol and the acetate ester of 1,4-diol and a top fraction containing acetic acid and materials having boiling point lower than that of acetic acid, a portion of the bottom fraction being returned to the first reaction zone and the rest being returned to the second reaction zone or any other preceding stage, (e) supplying the top fraction to a fourth distillation column to recover acetic acid and a portion of water as a bottom fraction and to obtain a top fraction containing the cyclic ether and water, the top fraction being supplied to a fifth distillation column operated under a pressure higher than that of the fourth distillation column to recover the cyclic ether as a bottom fraction and to distilled out a water-cyclic ether azeotrope being returned to any stage between the second column and the fourth column, and (f) supplying an acetate ester of a 1,4-diol raw material to any of steps (a) to (c).

According to this invention there is also provided a process for producing a cyclic ether and a 1,4-butanediol or 1,4-butenediol by reacting an acetate ester of 1,4-butanediol or 1,4-butenediol with water in the presence of a solid acid catalyst in a first reaction zone and second reaction zone, the improvement wherein said acetate ester of 1,4-butanediol or 1,4-butenediol contains an acetate ester of 1,2-butanediol or 1,2-butenediol and a 1,4-diol fraction containing the 1,2-diol, the acetate ester of 1,2-diol and the acetate esters of 1,4-diol from the second column is subjected to distillation to separate a top fraction containing the 1,2-diol and the acetate ester of 1,2-diol and a bottom fraction containing the 1,4-diol and the acetate ester of 1,4-diol, the former being removed and the latter being supplied to a second reaction zone containing a solid acid catalyst.

DETAILED DESCRIPTION OF THE INVENTION

Figure 1:
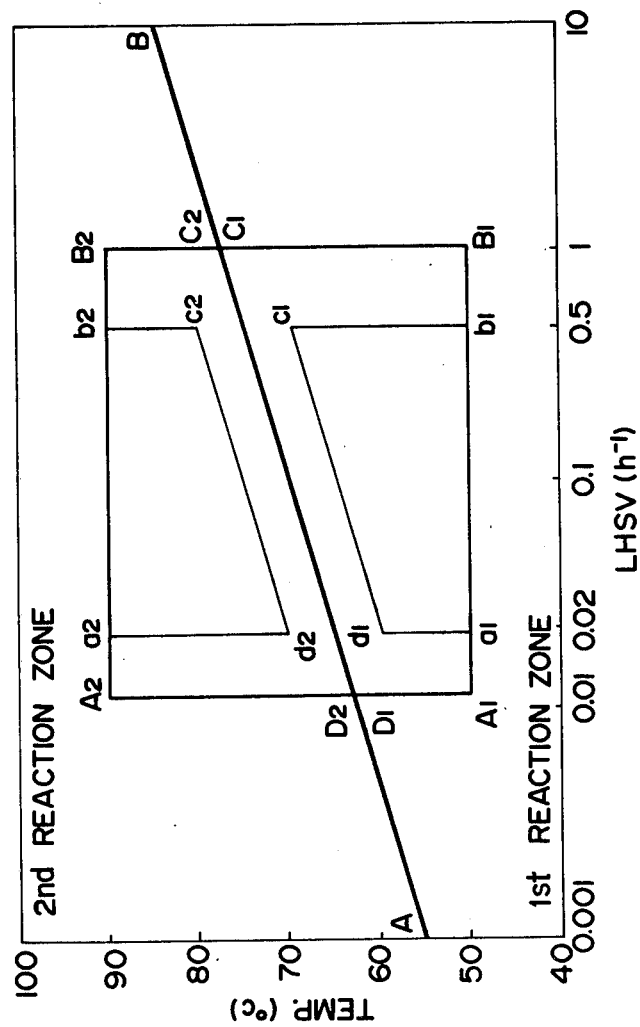
FIG. 1 shows relationship of the temperature and LHSV ($hr^{-1}$) of the first reaction zone and the second reaction zone using a cation exchange resin.

Acetate ester of 1,4-butanediol and 1,4-butendiol which may be used as the raw material according to this invention include, for example, mono- and di-acetate esters of a 1,4-diol, such as 1,4-diacetoxybutane, 1-hydroxy-4-acetoxybutane, 1,4-diacetoxybutene-2, and 1-hydroxy-4-acetoxybutene-2 (hereinafter refer to as "acetate ester" or "acetate ester of 1,4-diol").

Such acetate ester of 1,4-diol may be produced by various ways. One typical process is that butadiene, acetic acid and oxygen or a molecular oxygen-containing gas are reacted in the presence of a palladium catalyst to obtain an acetoxylation product from which desired 1,4-diacetoxybutene-2, and 1-hydroxy-4-acetoxybutene-2 are separated. They may be hydrogenated into 1,4-diacetoxybutane and 1-hydroxy-4-acetoxybutane.

The acetate ester product contains mainly above mentioned acetate esters, however, the product may contain isomers of acetate esters of 1,2- and/or 1,3-diols as well as acetic acid and butyracetate hydrogenation byproduct depending upon the operation and purification conditions. We have found that no separation of such byproduct may be required in carrying out the process of this invention.

Although 1-hydroxy-4-acetoxybutane may be obtained by partial hydrolysis of 1,4-diacetoxybutane, the preferred process is by reacting propylene, acetic acid and a molecular oxygen-containing gas in the presence of a palladium catalyst to obtain allyl acetate followed by subjecting the product in turn to an oxo reaction and hydrogenation. It is preferred to use the diacetate ester or the monoacetate ester containing more than 80% by weight of the 1,4-isomer as the raw material.

Water which is one of the raw materials according to this invention may be from any source and preferably free from chlorine ion.

The acetate raw material and water employed according to this invention may be either fresh materials or those recovered from any of the reaction steps so far as they do not contain low boiling byproducts, such as acetone, acrolein and n-butyraldehyde at a level of more than 20% by weight.

The catalyst which promotes hydrolysis and cyclization reactions is a solid acid catalyst including, for example, activated clay, silica titania, silica alumina, silica zirconia, chromia alumina, silica magnesia, natural and synthetic zeolite and a strong acid cation exchange resin. The most preferred is a strong acid cation exchange resin which is conveniently a sulfonic acid type cation exchange resin the matrix of which is a copolymer of styrene and divinyl benzene. The cation exchange resin may be either a gel type or a porous type, for example, DIAION SK1B, SK103, SK106, PK206, PK216 and PK228 available from Mitsubishi Chemical Industries, Limited, Tokyo, Japan.

The catalyst is conveniently used as a fixed bed in a reaction vessel. The vessel may be made of stainless steel of SUS 304 or more highgrade and SUS 316 is most preferred.

According to this invention, the acetate ester and water are reacted in the first reaction zone in the presence of the solid acid catalyst to effect hydrolysis to obtain a 1,4-diol. The temperature at which hydrolysis is effected is from 30° to 120° C., preferably 40° to 100° C. At lower temperature, the reaction rate considerably lowers with the result of requiring a large amount of the catalyst and at higher temperature the production of a hydrofuran, such as tetrahydrofuran and dihydrofuran in the first reaction zone increases.

The cyclization reaction in the presence of the catalyst in the second reaction zone is carried out at a temperature from 40° to 140° C., preferably 50° to 120° C.

Where the catalyst in both first and second reaction zones is a cation exchange resin, the liquid hourly space velocity (LHSV) and the reaction temperature in each zone are controlled so as to satisfy the relationship illustrated in FIG. 1. In FIG. 1, the region above line A–B is the temperature of the second zone and the region below the line is the first zone, preferably within the regions $A_1B_1C_1D_1$ and $A_2B_2C_2D_2$ and more preferably $a_1b_1c_1d_1$ and $a_2b_2c_2d_2$, respectively.

The pressure of each reaction zone is maintained at from 0 to 10 Kg/cm$^2$G.

In general, the hydrolysis reaction at a predetermined temperature reaches the equilibrium after a certain period has passed. At the equilibrium conditions a considerable amount of a monoacetate ester is unavoidably produced, and this is undesirable when the production of 1,4-diol is intended. The reaction rate of hydrolysis can be accelerated by raising the reaction temperature with a disadvantage of increase in production of tetrahydrofuran and other high boiling materials. When the hydrolysis is carried out at a low temperature and with a high water concentration, the yield of tetrahydrofuran decreases. Therefore, it is reasonable to expect that a yield predominantly of 1,4-diol will be obtained by effecting the hydrolysis at a lower temperature in the presence of a large amount of water without causing the production of undesirable tetrahydrofuran. However, this involves an inherent disadvantage in that a large amount of the unreacted diacetate ester and the partial hydrolysis product of monoacetate ester separated from the desired 1,4-diol should be circulated to the reaction system.

On the other hand, where the cyclization reaction forming a hydrofuran is carried out using an diacetate ester at relatively high temperature, for example at 80° C., the reaction rate is not effected to a considerable extent with the amount of water introduced into the reaction system. Further, when a monoacetate ester is used no additional water will be required from the theoretical point of view, and, in fact, the hydrofuran can be produced at a reasonable rate with addition of no or little water. However, diacetate ester is inevitably produced by a disproportionation which can be prevented by supplying a relatively large amount of water. It should be noted that the presence of water will adversely affect the reaction rate of the cyclization as mentioned above.

According to this invention, it has been found that the hydrolysis and the cyclization are successfully carried out separately in two reaction zones the conditions each of which are suitable for obtaining the desired product in each of the reactions. Thus, the monoacetate ester produced in the hydrolysis is utilized in the cyclization step as a raw material and the diacetate ester produced in the cyclization reaction is circulated to the hydrolysis step whereby the reaction rate in each step, especially in the cyclization is maintained at higher level without adversely affecting the yield. Further, with circulating the byproduct of each step to another step under predetermined conditions, the overall steam consumption required for distillation of the product can be saved.

In the process of this invention, it is not necessary to supply water as a raw material to the second reaction zone. Further, the presence of low boiling materials in water to be used in the process is permitted, and water obtained in acetoxylation process and containing low boiling materials, such as n-butyraldehyde can successfully be used in the first reaction zone.

This invention will be explained in more detail referring to attached drawings.

Figure 2:
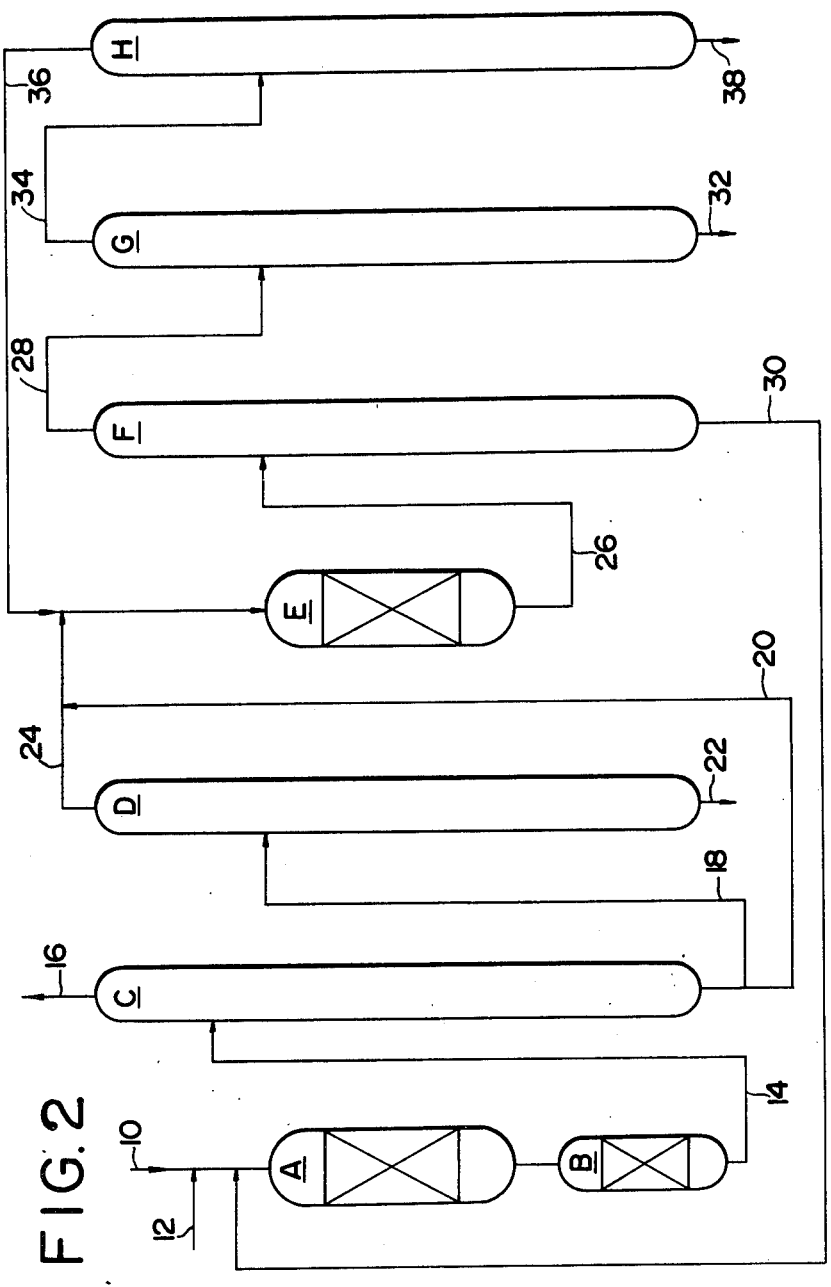
FIG. 2 shows a flow sheet of a preferred embodiment carrying out the process of this invention.

In FIG. 2, A is a reaction vessel packed with a solid catalyst, and acetate ester raw material via line 10, water via line 12 and the bottom fraction from third distillation column F via line 30 are supplied to the vessel A. The reaction product is introduced via line 14 to first distillation column C. If desired, the reaction product is treated in anion exchange resin bed B to remove sulfonate ion derived from a cation exchange resin catalyst.

The first column may have the number of theoretical plates (N. T. P.) of 5 to 20, preferably 7 to 14. The operation conditions are a head pressure of from 200 to 760 Torr., preferably 250 to 450 Torr., a bottom temperature of from 160° to 230° C., preferably 170° to 200° C. and more preferably 180° to 190° C. and a reflux ratio of from 0 to 2, preferably 0.01 to 0.5. The reaction product is introduced at the upper quarter region, preferably the second plate from the top in the case of a plate column. The top fraction containing water and acetic acid from the first distillation column is stripped off via line 16. The bottom fraction containing unreacted acetate ester, 1,4-butanediol and high boiling materials is withdrawn via line 18 and optionally a portion thereof is introduced via line 20 into second distillatin column D, and the rest is via line 20 supplied together with the top fraction from the second distillation column to second reaction vessel E. If the reaction product contains sufficiently large amount of 1,4-diol in comparison with the amount of 1,4-diol to be recovered as the product.

The second distillation column may have an N.T.P. of from 20 to 40, and is operated at a bottom temperature of from 160° to 230° C., preferably 170° to 200° C. and more preferably 180° to 190° C., under a head pressure of from 50 to 400 Torr., preferably 100 to 300 Torr. and a reflux ratio of from 1 to 5, preferably 2 to 4. The desired 1,4-diol product is recovered via line 22 from the second distillation column as a bottom fraction. The top fraction containing the unreacted acetate ester, a partial hydrolysis product and a small amount of butanediol is introduced via line 24 to second reaction vessel E to which the top fraction containing water and hydrofuran from fifth distillation column H is also supplied via line 36.

Second reaction vessel E is packed with a strong acid type cation exchange resin which promotes the conversion of the acetate ester into a hydrofuran. The reaction product containing hydrofuran, the unreacted acetate ester and partial hydrolysis product (monohydroxyacetate ester) is supplied via line 26 to third distillation column F having an N.T.P. of from 5 to 20, preferably 7 to 15, and is operated at a bottom temperature of from 150° to 220° C., preferably 170° to 190° C. under a head pressure of from 100 to 760 Torr., preferably 50 to 350 Torr. and at a reflux ratio below 1.0. In the third distillation column, the reaction product is separated into a top fraction containing hydrofuran, water and acetic acid and a bottom fraction containing the acetate ester and 1,4-diol, the former being transferred via line 28 to fourth distillation column and the latter being returned to the second reaction vessel or any other preceding stage, and preferably at least a portion thereof is returned to the first reaction vessel via line 30. The fourth distillation column has an N.T.P. of from 10 to 40, preferably 12 to 30, and is operated at a bottom temperature of from 110° to 150° C., under a pressure of from 0 to 3 Kg/cm$^2$G, the preferred conditions are under a pressure of 0 Kg/cm$^2$G and at a reflux ratio of from 0.5 to 5, especially at 1 to 3 to obtain a bottom fraction containing water and acetic acid which is withdrawn via line 32 and a top fraction containing mainly tetrahydrofuran which is supplied via line 34 to fifth distillation column H. The fifth distillation column has an N.T.P. of from 5 to 30 and is maintained under a pressure of from 3 to 20 Kg/cm$^2$, preferably 5 to 15 Kg/cm$^2$ higher than that of the fourth distillation column, that is, usually 3 to 23 Kg/cm$^2$G, preferably 5 to 18 Kg/cm$^2$G, the other conditions being a reflux ratio of 0.5 to 5 and a bottom temperature at from 100° to 180° C., preferably 130 to 160° C. A mixture of hydrofuran and water as a top fraction is returned via line 36 to the top of the second reaction vessel and the desired hydrofuran product is recovered as a bottom fraction via line 38.

When the raw material, diacetate ester of 1,4-diol, contains 1,2- and 1,3-isomers, it is necessary to separate the isomers. In such a case, separation column S is provided between the second distillation column and the second reaction vessel (FIG. 2). The top fraction of second distillation column is supplied via line 40 to the separation column. The separation column has an N.T.P. of from 20 to 40 and is operated at a bottom temperature of from 160° to 230° C., preferably 170° to 200° C. and more preferably 180° to 190° C., under a head pressure of from 10 to 400 Torr., preferably from 50 to 300 Torr. and at a reflux ratio of from 10 to 200.

The isomers are removed as a top fraction via line 42 and a bottom fraction is supplied via line 44 to the second reaction vessel. The isomers may be separated by using a second distillation column which has been modified to provide additional plates at the top region and removing a side cut.

According to this invention, a 1,4-diol and a hydrofuran can be produced in two separate reaction vessels and the proportion of the two products can be varied over a wide range in comparison with a case where the products are produced in a single reaction vessel. For example, a molar ratio of tetrahydrofuran to 1,4-butanediol of from 0.1:99.9 to 100:0 can be achieved.

Further, unreacted raw material from either reaction vessel can be supplied to another vessel, whereby recovery and circulation of unreacted raw material is easily accomplished with considerably less energy consumption. When the amount of butanediol produced is 0 to 4 times of tetrahydrofuran, especially 0 to 2 times in molar ratio, the energy consumption is minimized. For example, the expense including running cost and energy consumption required in carrying out this invention is about 80% or less in comparison with a process wherein a 1,4-diol and a hydrofuran are produced independently in two separate reaction vessels.

According to this invention, the presence of 1,2- and 1,3-isomers in the acetate ester raw material is permissible. This is beneficial from the point of view of economy.

Even though the raw materials which are circulated from the purification system to the reaction vessels contain a small amount of undesirable byproduct, the final products of 1,4-diol and hydrofuran obtained according to this invention do not contain such impurities and possess a high quality.

According to this invention, the acetate ester raw material may be supplied to any stage of from the first reaction vessel to the second reaction zone. In general, a raw material containing more diacetate ester may be supplied to the first reaction zone. Depending upon the proportion of diacetate ester, monoacetate ester and 1,4-diol, the raw material is supplied to a certain stage processing a material having a proportion closed to that of the raw material.

This invention will be explained in further detail by means of examples. However, it should be understood that this invention is in no way limited by these examples. In the examples, percentage and part are expressed by weight unless otherwise specifically defined.

EXAMPLE 1

Figure 3:
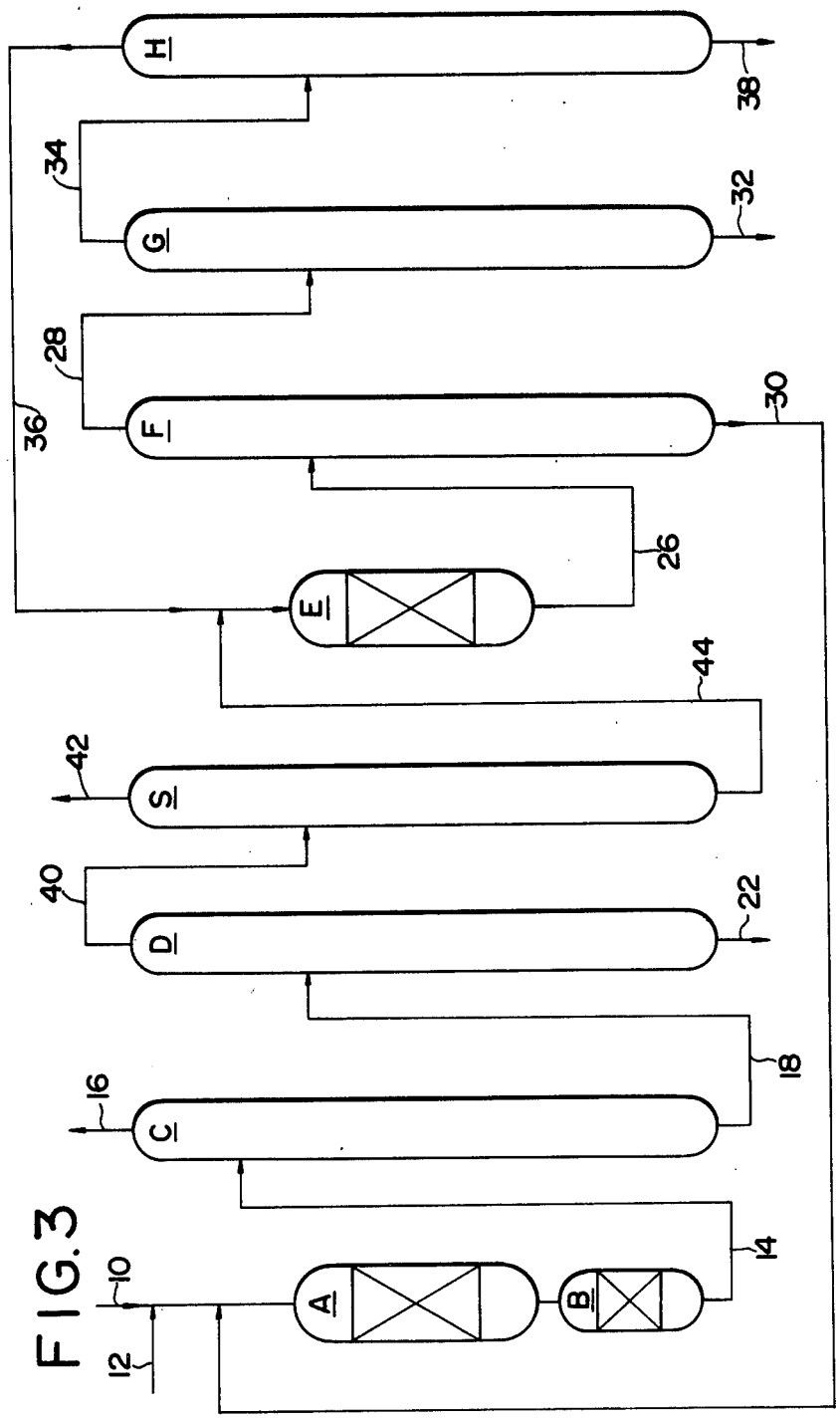
FIG. 3 shows a flow sheet of another embodiment.

This example was carried out using an apparatus as illustrated in FIG. 3.

The first reaction vessel A was made of stainless steel SUS 316. It had an internal diameter of 300 mm and a height of 1500 mm, and was packed with 50 l of a strong acid type cation exchange resin (DIAION SK1B available from Mitsubishi Chemical Industries, Limited, Tokyo, Japan). To the vessel A were supplied 4.11 Kg/hr. of acetate ester raw material having the following composition via line 10, 3.86 Kg/hr. of water containing 3.3% of acetic acid via line 12 and 4.10 Kg/hr. of a bottom fraction from the third distillation column F via line 30. The reaction was carried out at a temperature of 50° C.

Acetate ester raw material
1,4-diacetoxybutane: 88.5%
1,4-acetoxyhydroxybutane: 0.2%
1,2-diacetoxybutane: 8.2%
1,2-acetoxyhydroxybutane: 3.1%

The reaction product was passed through the anion exchange resin bed B packed with DIAION WA-20 available from Mitsubishi Chemical Industries, Limited to remove sulfonate ion and supplied via line 14 to the first distillation column C at 1 m below the top. The column C was made of stainless steel SUS 316. It had an internal diameter of 100 mm and a height of 5000 mm, it was packed with Dickson packings and operated at a bottom temperature of 185° C., under a head pressure of 300 Torr. and at a reflux ratio of 0.2. The top fraction containing 55.3% of water and 44.6% of acetic acid was removed via line 16 at a rate of 5.48 Kg/hr. and the bottom fraction containing mainly 1,4-butanediol and unreacted acetate ester was supplied via line 18 to the second distillation column D at 5 m below the top. The column D was similar to the column C but was 10 m in height and was operated at a bottom temperature of 195° C., under a head pressure of 200 Torr. and at a reflux ratio of 2.0. The bottom fraction containing at least 99% of 1,4-butanediol was recovered via line 22 at a rate of 0.95 Kg/hr. as the product and the top fraction having the following composition was supplied via line 40 to the separator S at 5 m below the top.

1,2-diacetoxybutane: 1.8%
1,4-diacetoxybutane: 27.4%
1,2-acetoxyhydroxybutane: 2.0%
1,4-acetoxyhydroxybutane: 57.7%
1,2-butanediol: 2.3%
1,4-butanediol: 8.8%

The separator S is similar to the column D and was operated at a bottom temperature of 185° C., under a head pressure of 250 Torr. and at a reflux ratio of 20. The top fraction comprising 1,2-isomers was removed via line 42 at a rate of 0.34 Kg/hr. The bottom fraction comprising 29.2% of 1,4-diacetoxybutane, 61.4% of 1,4-acetoxyhydroxybutane and 9.4% of 1,4-butanediol was withdrawn via line 44 at a rate of 5.29 Kg/hr. and combined with the top fraction from the fifth distillation column H via line 36 at a rate of 0.62 Kg/hr., and the mixture was supplied at 80° C. to the second reaction vessel E.

The vessel E was made of stainless steel SUS 316. It had an internal diameter of 300 mm and a height of 1500 mm and was packed with 60 l of H type strong acid cation exchange resin (DIAION SK1B available from Mitsubishi Chemical Industries, Limited, Tokyo, Japan). The reaction product was supplied via line 26 to the third distillation column F at 3 m below the top. The column F was similar to the column D and operated at a bottom temperature of 185° C. under a head pressure of 100 Torr. and at a reflux ratio of 0.5.

The bottom fraction comprising 49.6% of 1,4-diacetoxybutane, 42.0% of 1,4-acetoxyhydroxybutane and 8.4% of 1,4-butanediol was returned via line 30 to the first reaction vessel A at a rate of 4.10 Kg/hr. The top fraction comprising 71.3% of tetrahydrofuran, 8.8% of water and 19.9% of acetic acid was supplied via line 28 to the fourth distillation column G at 2.1 m below the top. The column G was similar to the column D and operated at a bottom temperature of 110° C., under a pressure of 0 Kg/cm$^2$G and at a reflux ratio of 2. The bottom fraction comprising 82.1% of acetic acid and 17.9% of water was removed via line 32 at a rate of 0.44 Kg/hr. The top fraction comprising 94.1% of tetrahydrofuran and 5.9% of water was supplied at a rate of 1.38 Kg/hr. via line 34 to the fifth distillation column H at 3.8 m below the top. The column H was similar to the column D and operated at a bottom temperature of 155° C. under a pressure of 7 Kg/cm²G and at a reflux ratio of 3. The bottom fraction containing at least 99.9% of tetrahydrofuran was recovered via line 38 at a rate of 0.76 Kg/hr. as the desired product and the top fraction comprising 87.0% of tetrahydrofuran and 13.0% of water was returned via line 36 to the second reaction vessel E at a rate of 0.62 Kg/hr.

EXAMPLE 2

The production was carried out using the apparatus used in Example 1 and illustrated in FIG. 3.

To the first reaction vessel A were supplied 4.09 Kg/hr. of acetate ester raw material having the following composition via line 10, 4.23 Kg/hr. of water containing 3.3% of acetic acid via line 12 and 3.16 Kg/hr. of the bottom fraction from the third distillation column F via line 30.

1,2-diacetoxybutene: 8.1%
1,2-acetoxyhydroxybutene: 3.0%
1,4-diacetoxybutene: 88.0%
1,4-acetoxyhydroxybutene: 0.2%
1,4-butenediol: 0.9%

The reaction product was supplied via line 14 to the first distillation column C at 1 m below the top. The column C was operated at a bottom temperature of 183° C., under a pressure of 380 Torr. and at a reflux ratio of 0.2. The top fraction comprising 58% of water and 42% of acetic acid was removed via line 16 at a rate of 5.86 Kg/hr. The bottom fraction containing mainly 1,4-butenediol and unreacted acetate ester was supplied via line 18 to the second distillation column D at 5 mm below the top. The column D was operated at a bottom temperature of 200° C., under a pressure of 200 Torr. and at a reflux ratio of 2.0.

The bottom fraction containing 90% of 1,4-dihydroxybutene was recovered via line 22 at a rate of 1.03 Kg/hr. The top fraction was supplied via line 40 to the separator S at 5 m below the top. The separator S was operated at a bottom temperature of 182° C., under a pressure of 230 Torr. and at a reflux ratio of 20. The top fraction comprising 1,2-isomers (1,2-diacetoxybutene, 1,2-acetoxyhydroxybutene, 1,2-butenediol, etc.) was removed via line 42 at a rate of 0.33 Kg/hr. The bottom fraction comprising 28% of 1,4-diacetoxybutene, 63% of 1,4-acetoxyhydroxybutene and 9% of 1,4-butenediol was withdrawn via line 44 at a rate of 4.34 Kg/hr. and combined with 0.60 Kg/hr. of the top fraction returned via line 36 from the fifth distillation column H, and the mixture was supplied at 80° C. to the second reaction vessel E which was packed with 80 l of cation exchange resin (DIAION SK1B available from Mitsubishi Chemical Industries, Limited, Tokyo, Japan). The reaction product was supplied via line 26 to the third distillation column F at 3.5 m below the top. The column F was operated at a bottom temperature of 180° C., under a pressure of 100 Torr. and at a reflux ratio of 0.5. The bottom fraction was returned at a rate of 3.16 Kg/hr. via line 30 to the first reaction vessel A. The top fraction comprising 70% of dihydrofuran, 9% of water and 21% of acetic acid was supplied at a rate of 1.71 Kg/hr. via line 34 to the fourth distillation column G at 2.3 m below the top. The column G was operated at a bottom temperature of 110° C., under a pressure of 0 Kg/cm²G and at a reflux ratio of 2.3. The bottom fraction comprising 82% of acetic acid and 18% of water was removed at a rate of 0.44 Kg/hr. via line 32. The top fraction comprising 94% of dihydrofuran and 6% of water was supplied at a rate of 1.27 Kg/hr. via line 34 to the fifth distillation column H at 4.0 m below the top. The column H was operated at a bottom temperature of 160° C., under a pressure of 10 Kg/cm²G and at a reflux ratio of 3.5. The desired product of dihydrofuran having a purity of at least 95% was recovered at a rate of 0.66 Kg/hr via line 38 as the bottom fraction.

The top fraction comprising 87% of dihydrofuran and 13% of water was withdrawn at a rate of 0.61 Kg/hr. via line 36 and returned to the second reaction vessel E.

EXAMPLE 3

Figure 4:
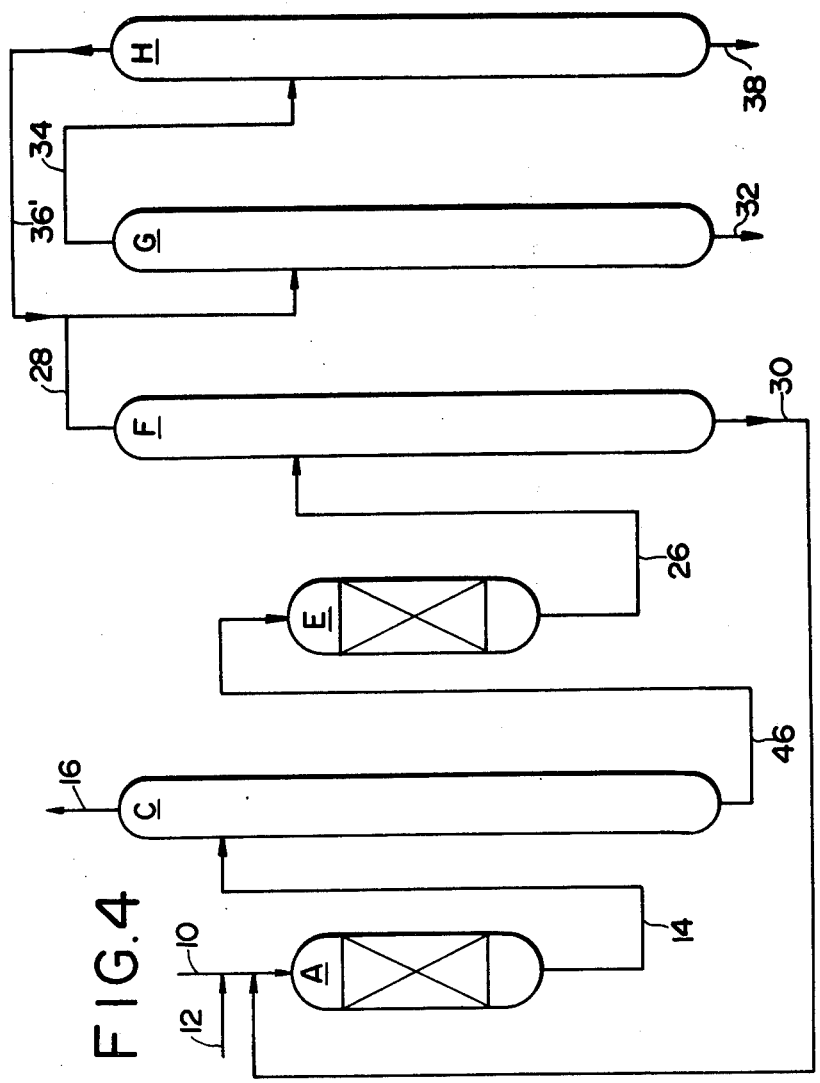
FIG. 4 shows a flow sheet of a further embodiment.

The apparatus employed was similar to that of Example 1 and was modified so as to connect the first distillation column C with the second reaction vessel E and return the top fraction of fifth distillation column H to the fourth distillation column G as shown in FIG. 4.

To the first reaction vessel A packed with 100 l of DIAION SK1B were supplied 3.48 Kg/hr. of 1,4-diacetoxybutane having a purity of at least 99.9% via line 10, 1.49 Kg/hr. of water containing 1% of n-butyraldehyde and 1% of acetic acid via line 12 and 21.27 Kg/hr. of the bottom fraction from the distillation column F via line 30. The hydrolysis was carried out at a temperature of 50° C.

The reaction product was supplied via line 14 to the first distillation column C at 1 m below the top. The column C was operated at a bottom temperature of 180° C., under a pressure of 370 Torr. and at a reflux ratio of 0.1. The top fraction having the following composition was removed via line 16 at a rate of 27.2 Kg/hr.

Water: 34.9%
Acetic acid: 64.7%
n-butyraldehyde: 0.4%

The bottom fraction having the following composition was supplied at a rate of 23.52 Kg/hr. via line 46 to the second reaction vessel E packed with 50 l of DIAION SK1B.

1,4-diacetoxybutane: 49.7%
1,4-hydroxyacetoxybutane: 41.5%
1,4-butanediol: 8.8%

The reaction product was supplied via line 26 to the distillation column F at 3.5 m below the top. The column F was operated at a bottom temperature of 180° C., under a head pressure of 100 Torr. and at a reflux ratio of 0.5. The bottom fraction comprising 57% of 1,4-diacetoxybutane, 36% of 1,4-hydroxyacetoxybutane and 7% of 1,4-butanediol was supplied at a rate of 21.27 Kg/hr. via line 30 to the first reaction vessel A. The top fraction comprising 63% of tetrahydrofuran, 7% of water and 30% of acetic acid was withdrawn at a rate of 2.25 Kg/hr. via line 28 and combined with 1.18 Kg/hr. of top fraction from the distillation column H via line 36' and the mixture was supplied to the distillation column G at 2.2 m below the top. The column G was operated at a bottom temperature of 110° C., under a pressure of 0 Kg/cm²G and at a reflux ratio of 2.5.

The bottom fraction comprising 81% of acetic acid and 19% of water was removed at a rate of 0.81 Kg/hr. via line 32, and the top fraction comprising 94% of tetrahydrofuran and 6% of water was supplied at a rate of 2.62 Kg/hr. via line 34 to the distillation column H at 3.8 m below the top. The column H was operated at a bottom temperature of 155° C., under a pressure of 7 Kg/cm²G and a reflux ratio of 3.0.

The desired product, tetrahydrofuran having a purity of at least 99%, was recovered at a rate of 1.44 Kg/hr. via line 38 and the top fraction comprising 87% of tetrahydrofuran and 13% of water was returned at a rate of 1.18 Kg/hr. via line 36' to the distillation column G.

EXAMPLE 4

Figure 5:
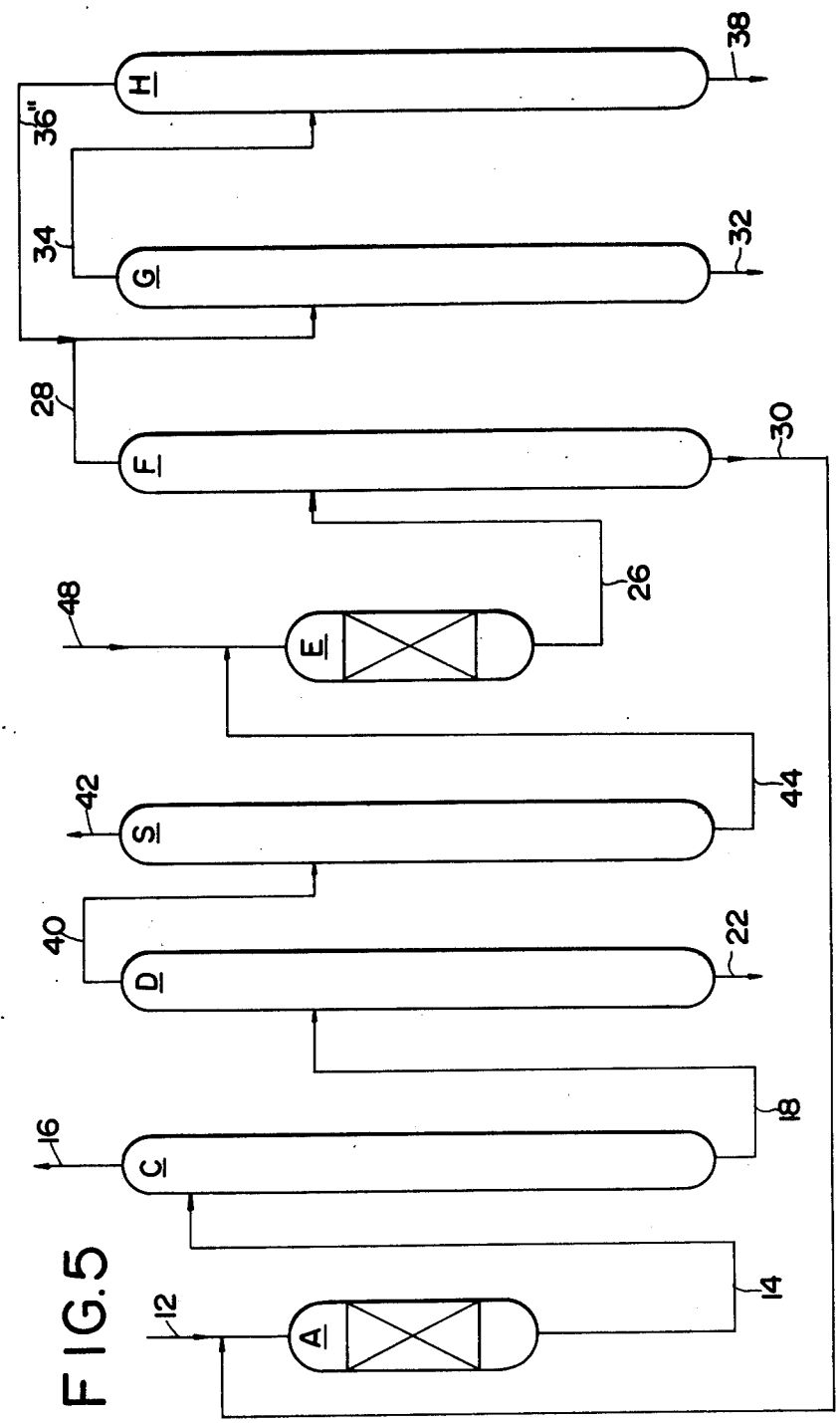
FIG. 5 shows a flow sheet of a still further embodiment.

The apparatus employed in this example was similar to that of Example 1 and was modified so as to supply the 1,4-hydroxyacetoxybutane raw material to the second reaction vessel and return the top fraction of the distillation column H to the distillation column G as shown in FIG. 5.

The first reaction vessel A packed with 30 l of DIAION SK1B was supplied with 1.62 Kg/hr. of water containing 1% of acetic acid via line 12 and 6.15 Kg/hr. of the bottom fraction from the distillation column F via line 30. The hydrolysis was carried out at 50° C.

The reaction product was supplied via line 14 to the fist distillation column C at 1 m below the top. The column C was operated at a bottom temperature of 180° C., under a pressure of 370 Torr. and at a reflux ratio of 0.1.

The top fraction comprising 57.1% of water and 42.9% of acetic acid was removed at a rate of 2.26 Kg/hr. via line 16. The bottom fraction comprising 23.3% of 1,4-diacetoxybutane, 52.1% of 1,4-hydroxyacetoxybutane, 24.1% of 1,4-butanediol and the remainder of others was supplied at a rate of 5.51 Kg/hr. via line 18 to the second distillation column D at 5 m below the top. The column D was operated at a bottom temperature of 195° C., under a pressure of 180 Torr. and at a reflux ratio of 2.2.

The desired product 1,4-butanediol having a purity of at least 99% as a bottom fraction was recovered via line 22 at a rate of 0.90 Kg/hr. and the top fraction was supplied via line 40 to the separator S at 5 m below the top. The separator was operated at a bottom temperature of 180° C., under a pressure of 200 Torr. and at a reflux ratio of 30.

From the top, undesirable impurities containing acetoxybutylaldehyde were removed at a rate of 0.03 Kg/hr. via line 42. The bottom fraction was withdrawn via line 44 at a rate of 4.58 Kg/hr. and combined with the 1,4-hydroxyacetoxybutane raw material containing 1% of acetoxybutyraldehyde supplied at a rate of 2.67 Kg/hr. via line 48 and the mixture was supplied to the second reaction vessel E packed with 15 l of DIAION SK1B. The reaction temperature was 80° C.

The reaction product was supplied via line 26 to the third distillation column F at 3 m below the top. The column F was operated at a bottom temperature of 180° C., under a pressure of 100 Torr. and at a reflux ratio of 0.7.

The bottom fraction having the following composition was returned at a rate of 6.15 Kg/hr. via line 30 to the first reaction vessel A.

1,4-diacetoxybutane: 26%
1,4-hydroxyacetoxybutane: 65%
1,4-butanediol: 9%

The top fraction comprising 65.4% of tetrahydrofuran, 8.2% of water and 26.4% of acetic acid was withdrawn at a rate of 1.10 Kg/hr. via line 28 and combined with the top fraction from the fifth distillation column H at a rate of 0.59 Kg/hr. via line 36", and the mixture was supplied to the fourth distillation column G at 2.1 m below the top. The column G was operated at a bottom temperature of 110° C., under a pressure of 0 Kg/cm$^2$G and at a reflux ratio of 2.7.

The bottom fraction comprising 76.3% of acetic acid and 23.7% of water was removed at a rate of 0.38 Kg/hr. via line 32.

The top fraction comprising 94% of tetrahydrofuran and 6% of water was supplied at a rate of 1.31 Kg/hr. via line 34 to the fifth distillation column H at 3.8 m below the top. The column H was operated at a bottom temperature of 155° C., under a pressure of 7 Kg/cm$^2$G and at a reflux ratio of 3.5.

From the bottom, the desired tetrahydrofuran product having a purity of at least 99% was recovered at a rate of 0.72 Kg/hr. via line 38. The top fraction comprising 87% of tetrahydrofuran and 13% of water was returned at a rate of 0.59 Kg/hr. via line 36" to the distillation column G.

We claim:

1. A process for producing a cyclic ether and 1,4-butanediol or 1,4-butenediol comprising reacting an acetate ester of 1,4-butanediol or 1,4-butenediol with water in the presence of an acid catalyst, the improvement comprising the steps of:
    (a) supplying a portion of the bottom fraction containing an acetic ester of a 1,4-diol from step (d) and water to a first reaction zone containing a solid acid catalyst to obtain a corresponding 1,4-diol,
    (b) supplying the reaction product to a first distillation column to distil out water and acetic acid and to obtain a bottom fraction containing the diol and the acetate ester,
    (c) supplying optionally a portion of the bottom fraction from the first distillation column to a second distillation column to recover the diol as a bottom fraction and supplying the top fraction containing the acetate ester together with the rest of the bottom fraction from the first distillation column to a second reaction zone containing a solid acid catalyst to obtain a corresponding cyclic ether,
    (d) supplying the reaction product from the second reaction zone to a third distillation column to obtain a bottom fraction containing the diol and the acetate ester of 1,4-diol and a top fraction containing acetic acid and low boiling materials, a portion of the bottom fraction being returned to the first reaction zone and the rest being returned to the second reaction zone or any other preceding stage,
    (e) supplying the top fraction to a fourth distillation column to recover acetic acid and a portion of water as a bottom fraction and to obtain a top fraction containing the cyclic ether and water, the top fraction being supplied to a fifth distillation column operated under a pressure higher than that of the fourth column to recover the cyclic ether as a bottom fraction and to distilled out a water-cyclic ether azeotrope being returned to any stage between the second column and the fourth column, and
    (f) supplying an acetate ester of a 1,4-diol to any of steps (a) to (c).

2. A process for producing cyclic ether and 1,4-butanediol or 1,4-butenediol according to claim 1, wherein said acetate ester of 1,4-butanediol or 1,4-butenediol contains an acetate esters of 1,2-butanediol or 1,2-butenediol and, in said step (c), 1,4-diol is recovered as a bottom fraction and a mixture of diols other than 1,4-diol and acetate esters of diols is distilled out and supplied to a separator in which a top fraction containing diols other than 1,4-diol and acetate ester thereof and a bottom fraction containing 1,4-diol and an acetate ester of 1,4-diol are obtained, the former being removed and the latter being supplied to a second reaction zone.

3. A process for producing a cyclic ether and 1,4-butanediol or 1,4-butenediol according to claim 1, wherein said solid acid catalyst is a strong acid type cation exchange resin.

4. A process for producing a cyclic ether and 1,4-butanediol or 1,4-butenediol according to claim 1, wherein the reaction temperature in said first reaction zone is from 40° to 100° C. and the reaction temperature of said second reaction zne is from 50° to 120° C.

5. A process for producing a cyclic ether and 1,4-butanediol or 1,4-butenediol according to claim 1, wherein the reaction temperatures and the liquid hourly space velocities in said first and second reaction zones are selected within the region $A_1B_1C_1D_1$ and the region $A_2B_2C_2D_2$ shown in FIG. 1, respectively.

6. A process for producing a cyclic ether and 1,4-butanediol or 1,4-butenediol according to claim 1, wherein the reaction temperatures and the liquid hourly space velocities of said first and second reaction zones are within the region $a_1b_1c_1d_1$ and the region $a_2b_2c_2d_2$ shown in FIG. 1, respectively.

7. A process for producing a cyclic ether and 1,4-butanediol or 1,4-butenediol according to claim 1, wherein the main component of said acetate ester raw material is a diacetate ester of a 1,4-diol and the diacetate ester is supplied to step (a).

8. A process for producing a cyclic ether and 1,4-butanediol or 1,4-butenediol according to claim 1, wherein the main component of said acetate ester raw material is monoacetate ester of a 1,4-diol and the monoacetate ester is supplied to step (c).

* * * * *